(12) United States Patent
Briancon

(10) Patent No.: US 7,003,335 B2
(45) Date of Patent: Feb. 21, 2006

(54) SENSING PHONE APPARATUS AND METHOD

(75) Inventor: Alain Charles Louis Briancon, Poolesville, MD (US)

(73) Assignee: InterDigital Technology Corporation, Wilmington, DE (US)

( * ) Notice: Subject to any disclaimer, the term of this patent is extended or adjusted under 35 U.S.C. 154(b) by 195 days.

(21) Appl. No.: 10/331,804

(22) Filed: Dec. 30, 2002

(65) Prior Publication Data

US 2004/0198432 A1 Oct. 7, 2004

(51) Int. Cl.
*H04M 1/00* (2006.01)
(52) U.S. Cl. .................... 455/575.6; 455/200; 455/420
(58) Field of Classification Search ............... 455/66.1, 455/556.1, 575.6, 90.1, 100, 128, 351, 67.11, 455/420, 423, 69; 600/502, 503, 509, 519, 600/481, 508
See application file for complete search history.

(56) References Cited

U.S. PATENT DOCUMENTS

| | | | |
|---|---|---|---|
| 5,772,586 A * | 6/1998 | Heinonen et al. ........... 600/300 |
| 6,231,519 B1 * | 5/2001 | Blants et al. ............... 600/529 |
| 6,238,338 B1 * | 5/2001 | DeLuca et al. ............. 600/300 |
| 6,381,482 B1 * | 4/2002 | Jayaraman et al. ......... 600/388 |
| 6,396,416 B1 * | 5/2002 | Kuusela et al. ........ 340/870.28 |
| 6,428,475 B1 * | 8/2002 | Shen .......................... 600/300 |
| 6,553,262 B1 * | 4/2003 | Lang et al. .................... 607/32 |
| 6,687,523 B1 * | 2/2004 | Jayaramen et al. ......... 600/388 |
| 2002/0077086 A1 * | 6/2002 | Tuomela et al. ............ 455/414 |
| 2004/0002634 A1 * | 1/2004 | Nihtila ....................... 600/300 |

* cited by examiner

*Primary Examiner*—Sonny Trinh
(74) *Attorney, Agent, or Firm*—Volpe and Koenig, P.C.

(57) ABSTRACT

Sensors measuring body conditions forward their data to a concentration point which transmits to a cellular phone through a wireless communication. The cellular phone incorporates a program which formats the data as a multimedia call. Information regarding status is transmitted using session initiated protocol or packet-based multimedia communications. The a second user's cellular phone is connected to a series of acupuncture needles connected to a cellular phone distributor through a network of thin electrical wires, which may be integrated into a wearable body item such as a glove, body shirt, full body garment, mask or the like. A program interprets the communication from the sending user and translates it into positive or negative stimuli.

24 Claims, 4 Drawing Sheets

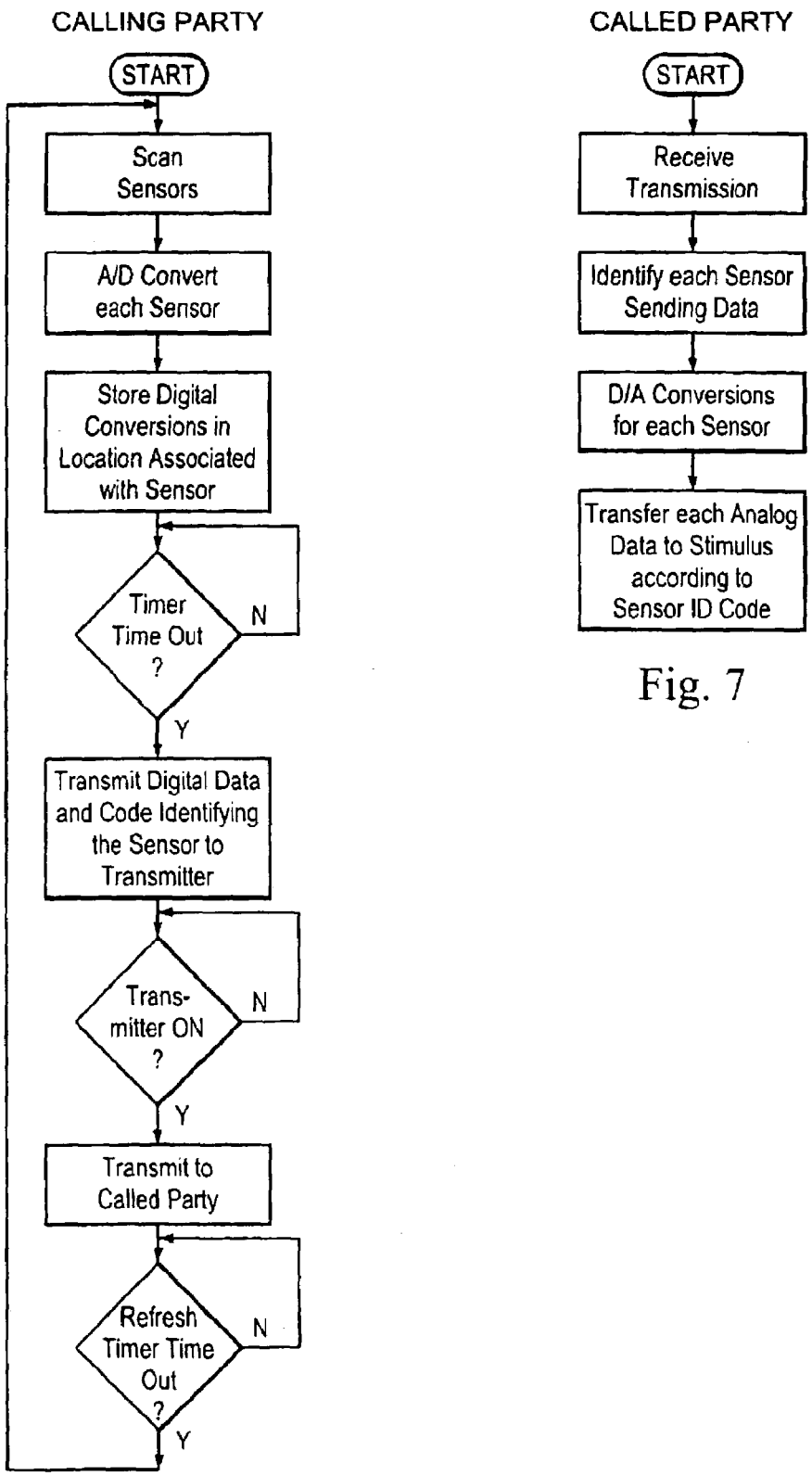

SENSING PHONE APPARATUS AND METHOD

FIELD OF INVENTION

The present invention relates to wireless communication between and among users. More particularly, the present invention relates to sensing physical and/or mental conditions of users and transmitting the sensed conditions to another connected user to provide electrical stimuli and/or sensations.

BACKGROUND

A number of applications have been developed in the cellular phone field to provide additional activities and services. As one example, a technique has been developed to provide a spectral analysis of a user's voice to estimate a stress level, which information is asked of the user. However, to date, the presentation of a feeling has merely been displayed and not sensed by another user.

SUMMARY

Sensors measure bodily conditions and convert them to a measurable signal. The signals are concentrated at a transmitter which wirelessly communicates with a handset. A program in the handset formats the data for transmission to a handset of another connected user. A program in the handset of the connected user converts the transmitted data and transfers the data to stimulation devices providing stimuli sensing the feelings of the sending subscriber.

BRIEF DESCRIPTION OF THE DRAWINGS

The invention will be understood upon a consideration of the accompanying specification and drawings wherein like elements are designated by like numerals, and wherein:

FIGS. 6 and 7 respectively show routines performed at the calling and called subscriber locations.

DETAILED DESCRIPTION OF THE PREFERRED EMBODIMENTS

Figure 1:
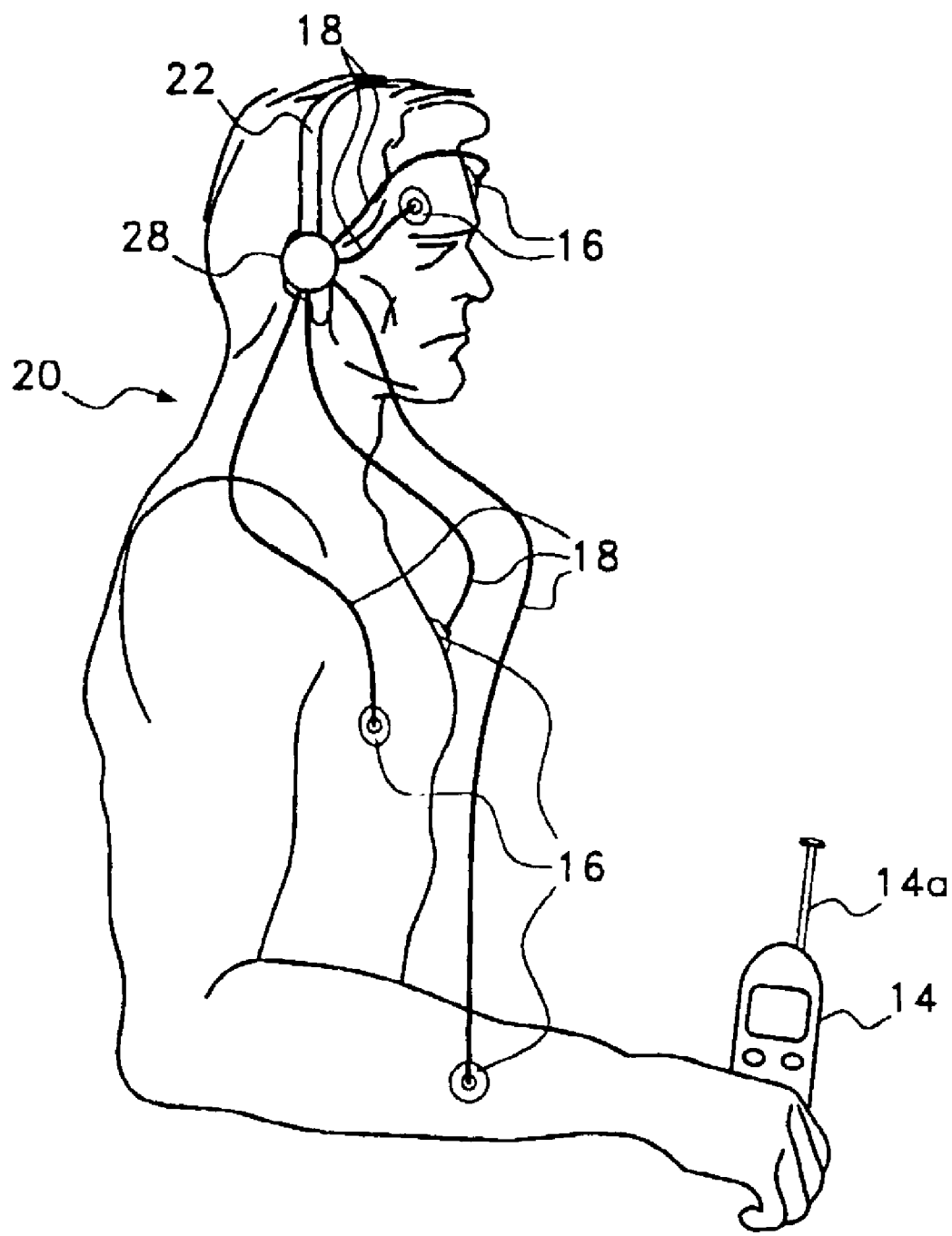
FIG. 1 shows an arrangement embodying the principles of the present invention in which conditions are sensed and transmitted.

FIG. 1 shows apparatus 10 of the present invention arranged on the body of an individual 12 and including cellular handset 14, a plurality of sensors 16 electrically coupled by wires 18 to a concentrator/transmitter 20 which may also include an earpiece and which is held upon the head of the user 12 by the headpiece 22.

The unit 20 collects/concentrates the signals received from the various sensors which may be located at any appropriate locations on the body, the locations on the head, chest and arm shown in FIG. 1 being merely exemplary.

The concentrator/transmitter 20 temporarily stores and then wirelessly transmits the data to handset 14, for example, using conventional equipment for wireless transmission. The signals received by handset 14 are formatted and transmitted as part of a multimedia communication according to the routine in FIG. 3.

User 12 incorporates the status information as part of the multimedia call. Information about status is sent using session initiated protocol (SIP) or H-323 (a standard for packet-based multimedia communications), for example. The detected signals are converted from analog to digital either in the sensor (item 16) or the concentrator (item 20).

The sensors 16 may be a variety of different sensing devices such as EKG/ECA wave sensors, tension elements similar to those used in lie detector tests, $CO_2$ sensors, etc.

Figure 5:
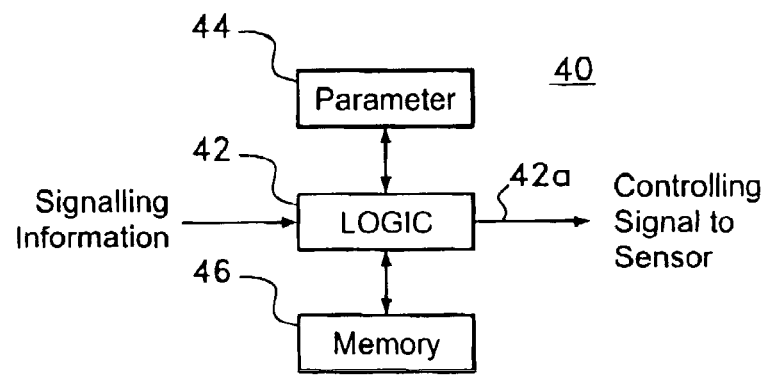

Handset 14 contains a program for formatting the data for transmission. One example is shown in FIG. 5. The handset 14 may include a built-in antenna or an extendable antenna such as the antenna 14a for transmission to a remote subscriber.

Data is sent as a set of packets transmitted in a manner similar to those employed in conventional wireless voice transmission.

Figure 2:
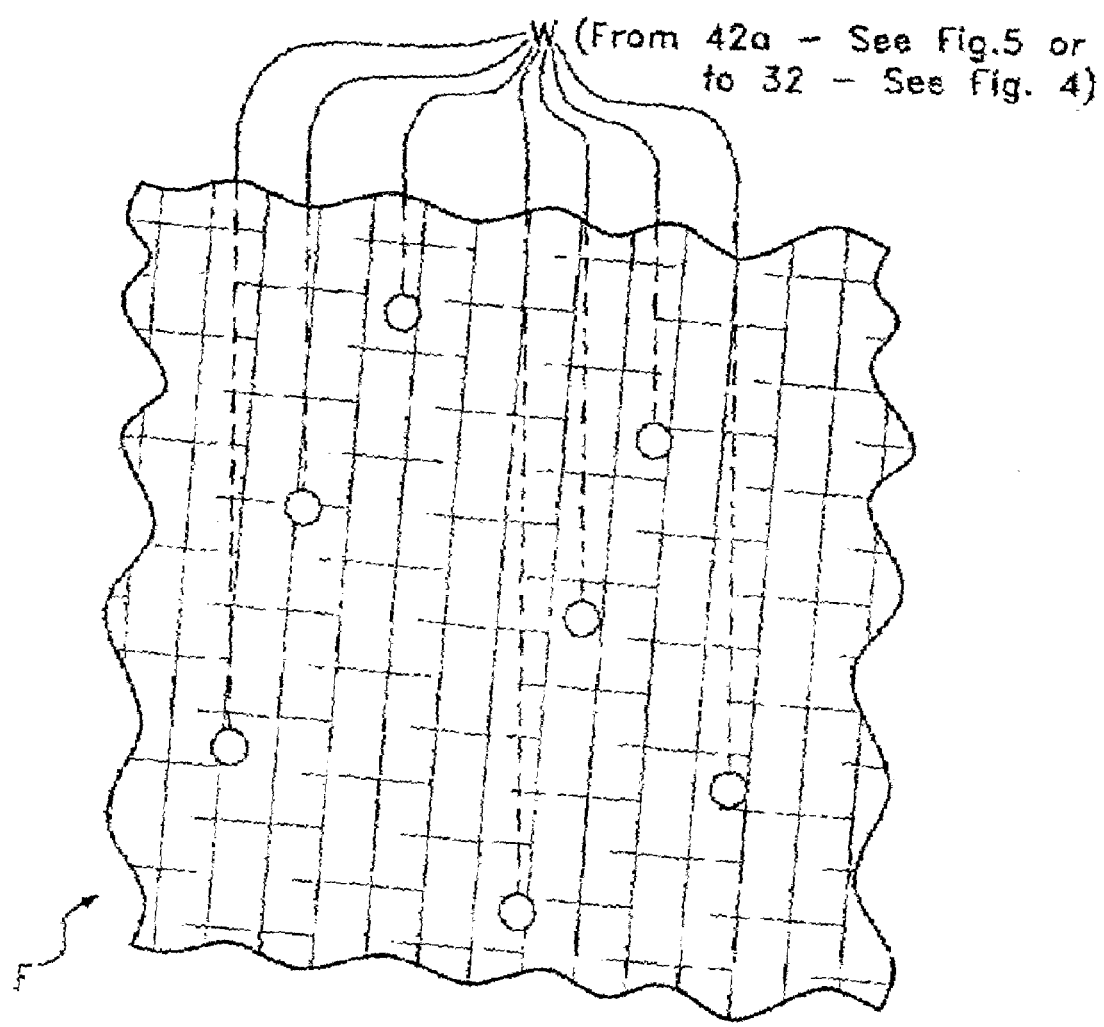
FIG. 2 shows a portion of a wearable item for respectively receiving/emitting physical/electrical stimuli.
Figure 3:
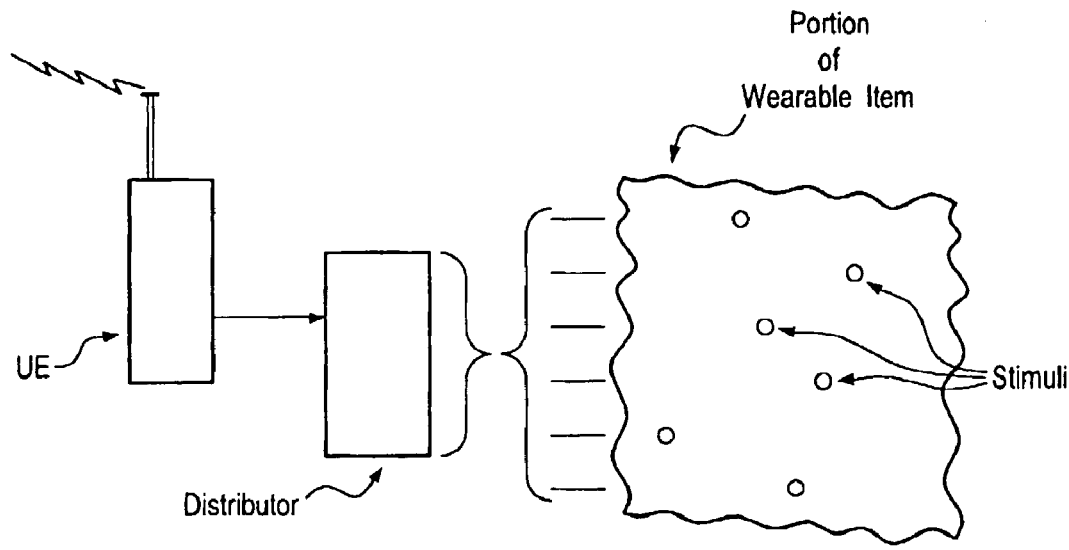
FIG. 3 shows an arrangement embodying the principles of the present invention in which the sensations detected, for example in FIG. 1, are received and converted into stimuli sensed by the receiving subscriber.

The cell phone 22 of the second user may, for example, be connected to a series of acupuncture needles, for example, connected to a network of thin electrical wires. A program implemented in Java or in another language interprets the signals from the user 12 of FIG. 1 and translates them into positive or negative stimuli, as shown in FIG. 3. FIG. 6 shows one example of a routine performed at the called subscriber location. The sensors shown in FIG. 1 may be arranged in a wearable item such as a glove, body shirt, length stocking or full body suit, which items are preferably worn tight to the body assure good electrical contact between the body and the sensors mounted within the wearable item. The wearable item shown as a portion of a fabric F in FIG. 2 has a network of wires W integrated into the wearable item and terminated at various locations in a stimulator tip to provide stimuli at a given location on the body of the wearer. The fabric portion may also be used to receive and convey stimuli from a sending user to a receiving user. The stimuli may be electrical or may be converted from an electric type stimuli through a converter such as an electromechanical converter converting the electrical signal to mechanical vibration, an electromechanical converter converting the electric signal to a temperature condition, an electrochemical converter to convert an electric signal to an aroma, etc.

The communications from the sender 12 may also be directed to a base station which may retransmit the communication to subscribers simultaneously with receipt or after a delay with the received communication being stored indefinitely.

Figure 4:
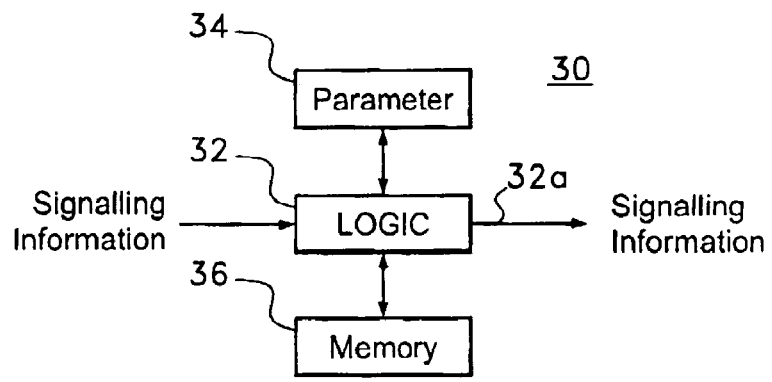
FIGS. 4 and 5 shows the devices employed for respectively collecting/transmitting and receiving/converting functions performed by the apparatus of FIGS. 1 and 3.

The apparatus 30, shown in FIG. 4, is employed for transmission. The sensed data is input to logic circuit 32. Parametric circuit 34 and memory 36 support logic circuit 32 in preparing data transmitted by the output 32a of logic circuit to the "called" party. See the routine shown in FIG. 6.

The apparatus 40 shown in FIG. 5 is employed for reception. The sensed data is input to logic circuit 42. Parametric circuit 44 and memory 46 support logic circuit 42 in preparing received data to be output at 42a of logic circuit 42. The output 42a couples the signals to the appropriate stimuli (see FIG. 2) through the distributor. See the routine shown in FIG. 7.

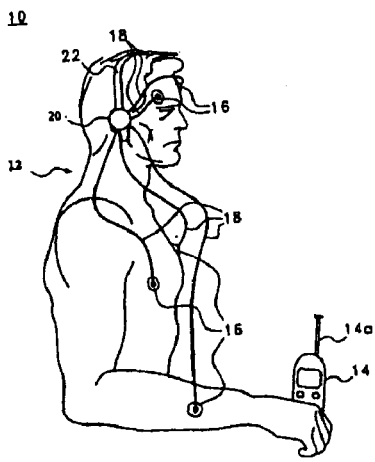

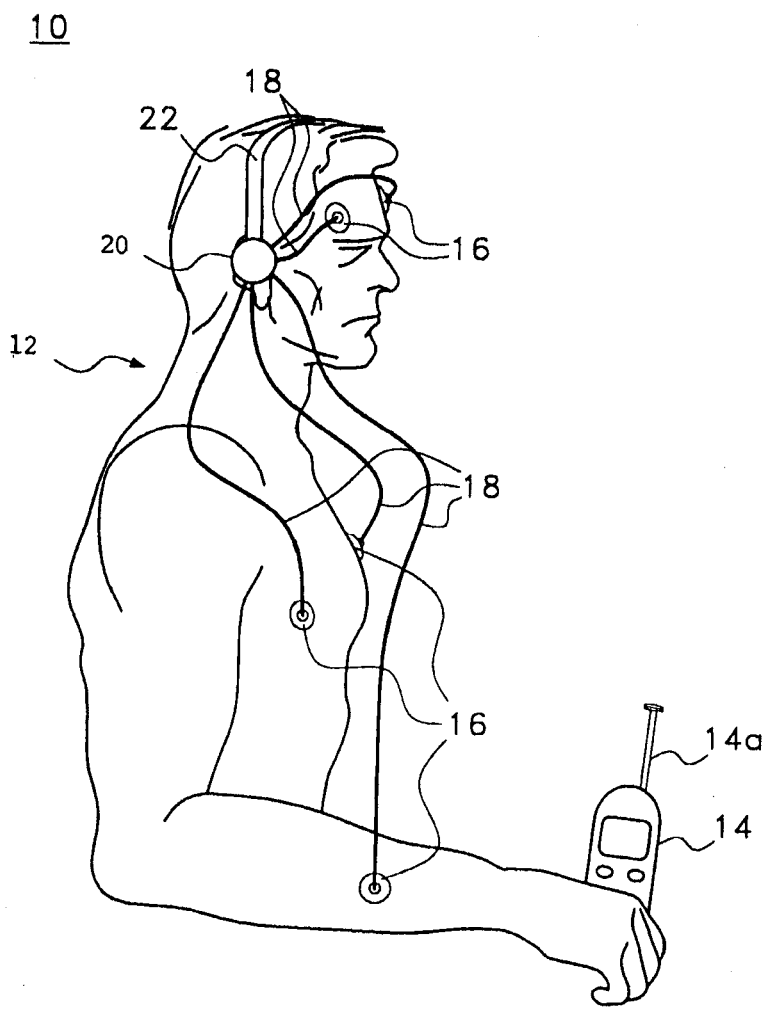

What is claimed is:

1. A method for transmitting physical conditions of a first user to a second user, employing wireless communication, comprising:
   (a) providing at least one first wearable item having a plurality of sensors integrated therein worn by said first user;
   (b) sensing conditions of said first user through the plurality of sensors;
   (c) processing the sensed conditions into data suitable for wireless transmission;
   (d) transmitting the data wirelessly to at least one remote device;
   (e) processing the transmitted data at a remote device for use as actuator inputs;
   (f) providing at least one second wearable item worn by said second user having a plurality of stimuli inducing members integrated therein; and
   (g) stimulating the second user by way of coupling the actuator inputs to the stimuli inducing members enabling the second user to perceive the transmitted conditions.

2. The method of claim 1 wherein step (b) includes sensing conditions employing mechanical sensors.

3. The method of claim 1 wherein step (b) includes sensing conditions employing electronic sensors.

4. The method of claim 1 wherein step (b) includes sensing conditions employing electromechanical sensors.

5. The method of claim 1 wherein step (b) includes sensing conditions employing chemical sensors.

6. The method of claim 1 wherein step (b) includes sensing conditions employing electrochemical sensors.

7. The method of claim 1 wherein step (b) includes sensing conditions employing physiological sensors.

8. The method of claim 1 wherein step (d) includes transmission of said data to a base station for subsequent retransmission.

9. A system for transmitting mental and physical conditions employing wireless communication, comprising:
   a first wearable item worn by a first user for sensing conditions of said first user through a plurality of sensors integrated into said first wearable item and arranged at a plurality of locations along said first wearable item;
   means for processing the sensed conditions into data; and
   means for transmitting the processed data to a remote device;
   a remote device for processing the transmitted data for use as actuator inputs; and
   a second wearable item worn by a second user for stimulating the second user by coupling the actuator inputs to stimuli inducing members integrated into said second wearable item enabling said second user to experience the transmitted conditions.

10. The apparatus of claim 9 wherein said sensors are mechanical sensors.

11. The apparatus of claim 9 wherein said sensors are electronic sensors.

12. The apparatus of claim 9 wherein said sensors are electromechanical sensors.

13. The apparatus of claim 9 wherein said sensors are chemical sensors.

14. The apparatus of claim 9 wherein said sensors are electrochemical sensors.

15. The apparatus of claim 9 wherein said sensors are physiological sensors.

16. The apparatus of claim 9 further includes a base station receiving said transmission for subsequent retransmission to the remote device.

17. The system of claim 9 wherein said first and second wearable items are gloves.

18. The system of claim 9 wherein said first and second wearable items are shirts.

19. The system of claim 9 wherein said first and second wearable items are stockings.

20. The system of claim 9 wherein said first and second wearable items are pairs of pants.

21. The system of claim 9 wherein said first and second wearable items are sleeves.

22. The system of claim 9 wherein the remote device comprises a mobile phone for receiving the transmitted data from the transmitter, and for processing the transmitted data for use as actuator inputs.

23. An apparatus for providing stimuli capable of being physically sensed by a person comprising:
   a first wearable item worn by a first user and having a plurality of sensors integrated therein;
   means for transmitting data representing physical conditions sensed by said plurality of sensors to a receiving device;
   said receiving device configured to receive the transmitted data;
   means for processing the transmitted data for use as actuator inputs;
   a second wearable item having a plurality of stimuli inducing members worn by a second user; and
   means for coupling the actuator inputs to the stimuli inducing members enabling said second user to experience the physical conditions; and
   wherein said second wearable item being of substantially a same type as said first wearable item, and wherein the plurality of stimuli inducing members are located in locations along said second wearable item corresponding to the locations of the plurality of sensors along said first wearable item.

24. Apparatus for communicating mental and physical sensations from a sender user to a remote user, comprising:
   means for sensing conditions of the sender user through a plurality of sensors;
   wireless sending means for transmitting the sensed conditions in a form compatible with the wireless sending means;
   remote receiving means for receiving said sensed conditions; and
   a plurality of means for applying stimuli to said remote user each associated with one of said sensed conditions.

* * * * *

UNITED STATES PATENT AND TRADEMARK OFFICE
CERTIFICATE OF CORRECTION

| | | |
|---|---|---|
| PATENT NO. | : 7,003,335 B2 | Page 1 of 3 |
| APPLICATION NO. | : 10/331804 | |
| DATED | : February 21, 2006 | |
| INVENTOR(S) | : Alain Charles Louis Briancon | |

It is certified that error appears in the above-identified patent and that said Letters Patent is hereby corrected as shown below:

The title page showing the illustrative figure should be deleted to be replaced with the attached title page.

On the Title page at Item (56), U.S. PATENT DOCUMENTS, page 1, right column, line 7, delete "6,687,523 B1 * 2/2004 Jayaramen et al. ..... 600/388"
and insert therefor --6,687,523 B1 * 2/2004 Jayaraman et al. ....... 600/388--.

The drawing sheet, consisting of Fig. 1 should be deleted to be replaced with the drawing sheet, consisting of Fig. 1 as shown on the attached pages.

Fig. 1 - Delete reference to "28" and insert therefor --20--.

Delete reference to "20", and insert therefore --12--.

At column 1, line 49, after "5", delete "shows" and insert therefor --show--.

At column 2, line 35, after the word "body" delete "assure" and insert therefor --assuring--.

In claim 9, line 49, delete "and".

In claim 23, line 40, delete "and".

Signed and Sealed this

Thirty-first Day of August, 2010

David J. Kappos
*Director of the United States Patent and Trademark Office*

(12) United States Patent
Briancon

(10) Patent No.: US 7,003,335 B2
(45) Date of Patent: Feb. 21, 2006

(54) SENSING PHONE APPARATUS AND METHOD

(75) Inventor: Alain Charles Louis Briancon, Poolesville, MD (US)

(73) Assignee: InterDigital Technology Corporation, Wilmington, DE (US)

(*) Notice: Subject to any disclaimer, the term of this patent is extended or adjusted under 35 U.S.C. 154(b) by 195 days.

(21) Appl. No.: 10/331,804

(22) Filed: Dec. 30, 2002

(65) Prior Publication Data
US 2004/0198432 A1    Oct. 7, 2004

(51) Int. Cl.
    H04M 1/00    (2006.01)
(52) U.S. Cl. .............. 455/575.6; 455/200; 455/420
(58) Field of Classification Search .......... 455/66.1, 455/556.1, 575.6, 90.1, 100, 128, 351, 67.11, 455/420, 423, 69; 600/502, 503, 509, 519, 600/481, 508
See application file for complete search history.

(56) References Cited

U.S. PATENT DOCUMENTS

| | | | |
|---|---|---|---|
| 5,772,586 A * | 6/1998 | Heinonen et al. | 600/300 |
| 6,231,519 B1 * | 5/2001 | Blants et al. | 600/529 |
| 6,238,338 B1 * | 5/2001 | DeLuca et al. | 600/300 |
| 6,381,482 B1 * | 4/2002 | Jayaraman et al. | 600/388 |
| 6,396,416 B1 * | 5/2002 | Kuusela et al. | 340/870.28 |
| 6,428,475 B1 * | 8/2002 | Shen | 600/300 |
| 6,553,262 B1 * | 4/2003 | Lang et al. | 607/32 |
| 6,687,523 B1 * | 2/2004 | Jayaramen et al. | 600/388 |
| 2002/0077086 A1 * | 6/2002 | Tuomela et al. | 455/414 |
| 2004/0002634 A1 * | 1/2004 | Nihtila | 600/300 |

* cited by examiner

Primary Examiner—Sonny Trinh
(74) Attorney, Agent, or Firm—Volpe and Koenig, P.C.

(57) ABSTRACT

Sensors measuring body conditions forward their data to a concentration point which transmits to a cellular phone through a wireless communication. The cellular phone incorporates a program which formats the data as a multimedia call. Information regarding status is transmitted using session initiated protocol or packet-based multimedia communications. The a second user's cellular phone is connected to a series of acupuncture needles connected to a cellular phone distributor through a network of thin electrical wires, which may be integrated into a wearable body item such as a glove, body shirt, full body garment, mask or the like. A program interprets the communication from the sending user and translates it into positive or negative stimuli.

24 Claims, 4 Drawing Sheets